United States Patent [19]

D'Silva

[11] 4,232,035
[45] Nov. 4, 1980

[54] CARBAMATE PESTICIDAL COMPOUNDS COMPOSITIONS AND METHODS OF USE

[75] Inventor: Themistocles D. J. D'Silva, South Charleston, W. Va.

[73] Assignee: Union Carbide Corporation, New York, N.Y.

[21] Appl. No.: 645,407

[22] Filed: Dec. 30, 1975

[51] Int. Cl.$^3$ .................... A01N 43/78; A01N 43/80; A01N 43/02; C07D 339/06
[52] U.S. Cl. .................................. 424/270; 424/246; 424/275; 424/276; 424/277; 549/14; 549/21; 549/30; 549/38; 549/68; 544/58.2; 548/190

[58] Field of Search ..................... 260/327 P, 306.7 T; 424/277, 246, 276, 275, 270; 544/58; 549/14, 21, 38, 68, 30

[56] References Cited

U.S. PATENT DOCUMENTS

| | | | |
|---|---|---|---|
| 3,223,733 | 12/1965 | Heiss et al. ............................ | 260/566 |
| 3,299,137 | 1/1967 | Payne et al. ........................... | 260/566 |
| 3,454,642 | 7/1969 | Friedman ............................... | 260/566 |

*Primary Examiner*—Leonard Schenkman
*Attorney, Agent, or Firm*—Clement J. Vicari

[57] ABSTRACT

Novel N-dithioalkyl and N-dithioaryl substituted cyclic carbamoyloximes exhibit exceptional pesticidal activity.

42 Claims, No Drawings

CARBAMATE PESTICIDAL COMPOUNDS COMPOSITIONS AND METHODS OF USE

This invention relates to novel N-dithioalkyl and N-dithioaryl substituted cyclic carbamoyloximes compounds, to their preparation and to their use in pesticidal compositions and for the control of certain economic pests.

More particularly, this invention relates to novel compounds corresponding to the following general formula:

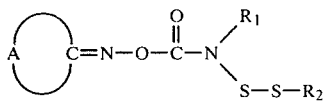

wherein:
$R_1$ is lower alkyl;
$R_2$ is alkyl, alkenyl, cycloalkyl, cycloalkenyl, bicycloalkyl, bicycloalkenyl, phenyl, phenylalkyl or phenyl or phenylalkyl substituted with one or more chloro, bromo, fluoro, nitro, cyano, alkyl, alkylthio, methylenedioxy, dialkylamino, trifluoromethyl, phenoxy, phenylthio substituents or a combination thereof;
A is a divalent aliphatic chain, completing a five or six membered alicyclic ring, which includes in any combination one or two divalent oxygen, sulfur, sulfinyl sulfonyl or amido group.

The novel N-dithioalkyl and N-dithioaryl substituted cyclic carbamoyloxime of this invention exhibit outstanding miticidal and insecticidal activity. Certain of the new compounds also exhibit excellent nematocidal activity. They are relatively non-toxic to plants and mammals when used in amounts sufficient to kill mites, insects and nematodes. In general, those compounds in which the combined total number of aliphatic carbons included in $R_1$, is 1, in $R_2$ is from 4 to 10 and/or in A is from 2 to 3 exhibit the highest level of pesticidal activity.

The preferred compounds of this invention are those in which $R_1$ is methyl.

The novel compounds of this invention can be prepared conveniently in accordance with the following reaction scheme;

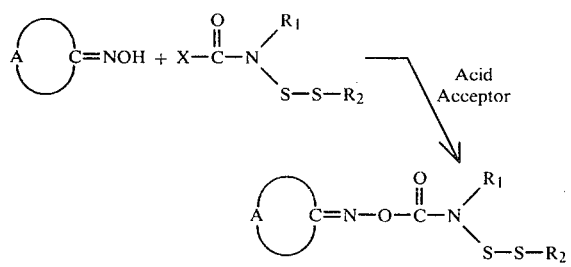

In the above equation $R_1$, $R_2$ and A are as described above. X may be either chlorine or fluorine. Equivalent amounts of the oxime, carbamoyl halide and an acid acceptor are reacted preferably in an inert solvent. Suitable inert solvents include benzene, toluene, xylene, dioxane, tetrahydrofuran, ethyl ether, methylene chloride and the like. The acid acceptor employed can be either an organic or inorganic base. Suitable inorganic bases include alkali metal hydroxides such as sodium or potassium hydroxide. When an inorganic base is employed as an acid acceptor, the reaction may be conducted in either a single phase system or a two phase system. In either case a phase transfer agent, such as a crown ether o a quaternary ammonium halide, be used to facilitate the transfer of reactants across the interface. The organic bases which are useful include tertiary amines such as triethylamine, and 1,4-diazabicylo [2.2.1] octane. Trimethyl amine, and pyridine are preferred acid acceptors.

The reaction temperature and pressure are not critical. The reaction goes essentially to completion at room temperature. Elevated temperatures may be employed if it is desired to reduce the reaction time. The reaction is generally conducted at atmospheric or autogenous pressure.

The oxime precursors used in the preparation of the novel compounds of this invention may be prepared by conventional means as, for example, by the methods described in U.S. Pat. Nos. 3,217,036, 3,217,037, 3,400,153, 3,536,760 and 3,576,834.

The carbamic acid halide precursors used in the preparation of the novel compounds according to this invention are preferably prepared according to the following reaction scheme:

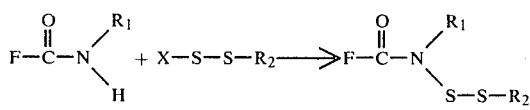

$R_1$, and $R_2$ are as described above and X is chlorine. The above reaction scheme and other reaction schemes which can also be utilized to prepare the carbamic acid halide precursors are described in more detail in U.S. patent application Ser. No. 486,631.

The following specific examples are presented to more particularly illustrate the manner in which the new compounds of this invention may be prepared, and are not to be construed as a limitation on the scope of this invention.

EXAMPLE I

Preparation of 2-[[O-[N-Methyl-N-(2-methyl-2-propanethiosulfenyl) carbamoyl]oximino]]-3,5,5-trimethylthiazo lidin-4-one.

To a solution of 5.27 g (0.03 m) of 3,5,5-trimethyl-2-oximino-thiazolidin-4-one and 10 g of a 50% solution of N-methyl-N-(2-methyl-2-propanethiosulfenyl) carbamoyl fluoride in 100 ml. of dioxane was added 3.1 g (0.03 m) of triethylamine. After stirring at ambient temperature for 16 hrs., the reaction mixture was diluted with 200 ml. of water and extracted in ethyl acetate. The organic extract was washed with water, dried over magnesium sulfate and concentrated under reduced pressure. 2-[[O-[N-Methyl-N-(2-Methyl-2-propanethiosulfenyl) carbamoyl]-oximino]]-3,5,5-trimethyl-thiazolidin-4-one crystallized on addition of hexane. Recrystallization from a isopropylether and hexane solution yielded 3.0 g of a white solid m.p. 71°–73° C. m/e=35.

Calc'd for $C_{12}H_2N_3O_3S_3$: C, 41.00; H, 6.02; N, 11–95. Found: C, 40.83; H, 5.91; N, 12.08.

EXAMPLE II

Preparation of
2-[[O-[N-Methyl-N-(2-methyl-2-propanethiosulfenyl)-carbamoyl]oximino]]-1,4-dithiane.

To a solution of 2.33 g (0.016 m) of 2-oximino-1,4-dithiane and 6.69 g of a 50% solution of N-methyl-N-(2-methyl-2-propanethiosulfenyl) carbamoyl fluoride in 50 ml of dioxane, was added 1.58 g (0.016 m) of triethylamine. After stirring for 20 hrs. the reaction mixture was diluted with water and ethyl acetate and the organic extract was washed with water, dried and concentrated to an oil.

Calc'd for $C_{10}H_{18}N_2O_2S_4$: C, 36.78; H, 5.56; N, 8.58. Found: C, 36.31; H, 5.39; N, 7.99.

EXAMPLE III

Preparation of 4-[[O-[N-Methyl-N-(n-octylthiosulfenyl) carbamoyl]oximino]]-5-methyl-1,3-oxathiolane To a solution of 2.64 g (0.02 m) of 5-methyl-4-oximino-1,3-oxathiolane and 5.07 g (0.02 m) of N-methyl-N-(-octylthiosulfenyl)carbamoyl fluoride in 25 ml of dioxane was added 2.02 g (0.02 m) of triethylamine. After stirring for 20 hrs. the reaction mixture containing 4-[[O-[N-Methyl-N-(-octylthiosulfenyl)carbamoyl]oximino]]-5-methyl-1,3-oxathiolane was diluted with 100 ml of water and extracted in ethyl acetate. The organic extract was washed with dilute sodium hydroxide followed by dilute acid and water, dried over magnesium sulfate and concentrated to 6.3 g of a residual oil. Purification by column chromatography using silica gel yielded 3.3 g of an oil.

Calc'd for $C_{14}H_{26}N_2O_3S_3$: C, 45.87; H, 7.14; N, 7.64. Found: C, 45.78; H, 6.87; N, 7.56.

EXAMPLE IV

Preparation of
4-[[O-[N-Methyl-N-(methylthiosulfenyl)carbamoyl]oximino]]-5-methyl-1,3-oxathiolane.

To a solution of 4.22 g (0.032 m) of 5-methyl-4-oximino-1,3-oxathiolane and 5.0 g (0.032 m) of N-methyl-N-(methylthiosulfenyl) carbamoyl fluoride in 25 ml of dioxane was added 3.25 g (0.032 m) of triethylamine. After stirring at room temperature for 19 hrs. the reaction mixture was quenched with 100 ml of water and extracted in ethyl acetate. After the usual work-up it yielded a residual oil. Addition of isopropyl ether resulted in the precipitation of 0.16 g of a solid biscarbamate. The concentrated filtrate was purified by column chromatography to yield 2.97 g of an oil.

$N_D^{25}$ 1.5688.

Calc'd for $C_7H_{12}N_2O_3S_3$: C, 31.32; H, 4.51; N, 10.44. Found: C, 31.03; H, 4.47; N, 10.18.

EXAMPLE V

Preparation of
4-[[O-[N-Methyl-N-2-(2-methylpropanethiosulfenyl) carbamoyl]oximino]]-5-methyl-1,3-oxathiolane 4-[[O-[N-Methyl-N(2-methyl-2-propanethiosulfenyl)-carbamoyl]oximino]]-5-methyl-1,3-oxathiolane was prepared by the procedure described in Example III by reacting 2.85 g (0.0214 m) of 5-methyl-4-oximino-1,3-oxathiolane with 4.23 g (0.02 4 m) of N-methyl-N-(t-butylthiosulfenyl) carbamoyl fluoride and 2.17 g (0.0214 m) of triethylamine in 50 ml. of dioxane. The residual oil was purified using silica gel column.

Calc'd for $C_{10}H_{18}N_2O_3S_3$: C, 38.68; H, 5.84; N, 9.03. Found: C, 37.86; H, 5.80; N, 8.29.

EXAMPLE VI

Preparation of
4-[[O-[N-methyl-N-2-(propanethiosulfenyl)carbamoyl]oximino]]-5-methyl-1,3-oxathiolane To a solution of 5.0 g (0.0375 m) of 5-methyl-4-oximino-1,3-oxathiolane and 6.88 g (0.0375 m) of N-methyl-N-2-(propanethiosulfenyl) carbamoyl fluoride in 100 ml of benzene was added 2.44 g (0.0575 m) of pulverized potassium hydroxide and approximately 0.02 g of dicyclohexyl-18-crown-6. After stirring for 3 hr. at room temperature the reaction mixture was diluted with additional 50 ml of benzene and the benzene solution was washed with water, dried over magnesium sulfate and concentrated to an oil. 4-[[O-[N-Methyl-N-2-(propanethiosulfenyl)carbamoyl]oximino]]-5-methyl-1,3-oxathiolane crystallized on addition of isopropyl ether and hexane. It was recrystallized from isopropyl ether to yield 3.3 g of a white solid, m.p. 56°–58° C.

Calc'd for $C_9H_{16}N_2O_3S_3$: C, 36.46; H, 5.44; N, 9.45. Found: C, 36.37; H, 5.41; N, 9.40.

EXAMPLE VII

Preparation of
4-[[O-[N-methyl-N-(phenylthiosulfenyl)carbamoyl]oximino]]-5-methyl-1,3-oxathiolane.

4-[[O-[N-Methyl-N-(phenylthiosulfenyl)carbamoyl]oximino]]-5-methyl-1,3-oxathiolane was prepared by the procedure described in Example I by reacting 5.0 g (0.0375 m) of 5-methyl-4-oximino-1,3-oxathiolane, 8.15 g (0.0375 m) of N-methyl-N-(phenylthiosulfenyl) carbamoyl fluoride and 3.79 g (0.0375 m) of triethylamine in 100 ml of dioxane. The crude residual oil was purified using silica gel column to yield 3.5 g of an oil.

Calc'd for $C_{12}H_{14}N_2O_3S_3$: C, 43.61; H, 4.27; N, 8.48. Found: C, 43.70; H, 4.25; N, 8.57.

EXAMPLE VIII

Preparation of
4-[[O-[N-methyl-N-(4-methylphenylthiosulfenyl)carbamoyl]oximino]]-5-methyl-1,3-oxathiolane.

4-[[O-[N-Methyl-N-(4-methylphenylthiosulfenyl)carbamoyl]oximino]]-5-methyl-1,3-oxathiolane was prepared by the procedure described in Example I by reacting 4.0 g (0.03 m) of 5-methyl-4-oximino-1,3-oxathiolane, 6.95 g (0.03 m) of N-methyl-N-(4-methylphenylthiosulfenyl) carbamoyl fluoride and 3.07 g (0.03 m) of triethylamine in 50 ml of dioxane. The crude residual oil (7.3 g) was purified by dry column chromatography using silica gel.

Calc'd for $C_{13}H_{16}N_2O_3S_3$: C, 45.32; H, 4.68; N, 8.13. Found: C, 44.95; H, 4.57; N, 7.83.

EXAMPLE IX

Preparation of
4-[[O-[N-methyl-N-(4-chlorophenylthiosulfenyl)carbamoyl]oximino]]-5-methyl-1,3-oxathiolane.

4-[[O-[N-Methyl-N-(4-chlorophenylthiosulfenyl)carbamoyl]oximino]]-5-methyl-1,3-oxathiolane was prepared according to the procedure described in Example I by reacting 4.0 g (0.03 m) of 5-methyl-4-oximino-1,3-oxathiolane, 7.55 g (0.03 m) of N-methyl-N-(4-chlorophenylthiosulfenyl)carbamoyl fluoride and 3.07 g (0.03 m) of triethylamine in 50 ml of dioxane. Addition of isopropyl ether and ethyl acetate to the residual oil and cooling yielded 2.37 g of a white solid, m.p. 71°–73° C.

Calc'd for $C_{12}H_{13}Cl\ N_2O_3S_3$: C, 39.49; H, 3.59; N, 7.68. Found: C, 39.46; H, 3.54; N, 7.69.

EXAMPLE X

Preparation of 2-[[O-[N-methyl-N-(2-propanethiosulfenyl)carbamoyl]oximino]]-3,5,5-trimethylthiazolidin-4-one.

To a solution of 5.0 g (0.0287 m) of 3,5,5-trimethyl-2-oximinothiazolidin-4-one and 5.26 g (0.0287 m) of N-methyl-N-(2-propanethiosulfenyl) carbamoyl fluoride in 100 ml of benzene and 5 ml of acetonitrile, was added 1.86 g (0.0287 m) of pulverized potassium hydroxide and 0.02 g of dicyclohexyl-18-crown-6. After stirring the reaction mixture for 3 hrs. at room temperature, an additional 50 ml of benzene was added. The reaction mixture was quenched with water and the benzene layer was further washed with water, dried and concentrated. The residual oil was taken in isopropyl ether. On cooling 2-[[O-[N-methyl-N-(2-propanethiosulfenyl)carbamoyl]oximino]]-3,5,5-trimethylthiazolidin-4-one crystallized to yield 2.61 g of a white solid, mp 68°–69° C.

Calc'd for $C_{11}H_{19}N_3O_3S_3$: C, 39.15; H, 5.67; N, 12.45. Found: C, 39.12; H, 5.71; N, 12.39.

EXAMPLE XI

Preparation of 2-[[O-[N-methyl-N-(-butylthiosulfenyl)carbamoyl]oximino]]-3,5,5-trimethylthiazolidin-4-one.

2-[[O-[N-Methyl-N-(-butylthiosulfenyl)carbamoyl]oximino]]-3,5,5-trimethylthiazolidin-4-one was prepared according to the procedure described in Example X by reacting 3.48 g (0.02 m) of 3,5,5-trimethyl-2-oximino thiazolidin-4-one with 3.96 g (0.02 m) of N-methyl-N-(-butylthiosulfenylcarbamoyl fluoride and 1.3 g (0.02 m) of pulverized potassium hydroxide and 0.02 g of crown ether. The residual oil was taken in pentane and chilled to yield 5.0 g of a white solid, m.p. 36°–37° C.

Calc'd for $C_{12}H_{21}N_3O_3S_3$: C, 41.00; H, 6.02; N, 11.95. Found: C, 40.93; H, 6.00; N, 11.96.

EXAMPLE XII

Preparation of 2-[[O-[N-methyl-N-(cyclohexylthiosulfenyl)carbamoyl]oximino]]-3,5,5-trimethylthiazolidin-4-one 2-[[O-[N-Methyl-N-(cyclohexylthiosulfenyl)carbamoyl]oximino]]-3,5,5-trimethylthiazolidin-4-one was prepared according to the procedure described in Example X by reacting 3.48 g (0.02 m) of 3,5,5-trimethyl-2-oximino thiazolidin-4-one with 4.47 g (0.02 m) of N-methyl-N-(cyclohexylthiosulfenyl) carbamoyl fluoride and 1.32 g (0.02 m) of potassium hydroxide. Weight of 2-[[O-[N-methyl-N-(cyclohexylthiosulfenyl)carbamoyl]oximino]]-3,5,5-trimethylthiazolidin-4-one produced was 3.1 g. m.p. 86°–88° C.

Calc'd for $C_{14}H_{23}N_3O_3S_3$: C, 44.54; H, 6.14; N, 11.13. Found: C, 44.50; H, 6.13; N, 11.13.

EXAMPLE XIII

Preparation of 2-[[O-[N-methyl-N-(phenylthiosulfenyl)carbamoyl]oximino]]-3,5,5-trimethylthioazolidin-4-one 2-[[O-[N-Methyl-N-(phenylthiosulfenyl)carbamoyl]oximino]]-3,5,5-trimethylthiazolidin-4-one was prepared according to the procedure described in Example I, by reacting 5.0 g (0.0287 m) of 3,5,5-trimethyl-2-oximinothiazolidin-4-one, 6.24 g (0.0287 m) of N-methyl-N-(phenylthiosulfenyl)carbamoyl fluoride and 2.9 g (0.0287 m) of triethylamine in 100 ml of dioxane. 2-[[O-[N-Methyl-N-(phenylthiosulfenyl)carbamoyl]oximino]]-3,5,5-trimethylthiazolidin-4-one was crystallized from isopropyl ether to yield 7.0 g of a white solid. m.p. 73°–74° C.

Calc'd for $C_{14}H_{17}N_3O_3S_3$: C, 45.26; H, 4.61; N, 11.31. Found: C, 44.87; H, 4.47; N, 11.34.

EXAMPLE XIV

Preparation of 2-[[O-[N-methyl-N-(4-methylphenylthiosulfenyl)carbamoyl]oximino]-3,5,5-trimethylthiazolidin-4-one 2-[[O-[N-Methyl-N-(4-methylphenylthiosulfenyl)carbamoyl]oximino]]-3,5,5-trimethylthiazolidin-4-one was prepared according to the procedure described in Example I, by reacting 5.0 g (0.0287 m) of 3,5,5-trimethyl-2-oximino thiazolidin-4-one, 6.64 g (0.028 m) of N-methyl-N-(4-methylphenylthiosulfenyl)carbamoyl fluoride and 2.9 g (0.0287 m) of triethylamine in 50 ml of dioxane. 2-[[O-[N-Methyl-N-(4-methylphenylthiosulfenyl)carbamoyl]oximino]]-3,5,5-trimethylthiazolidin-4-one was crystallized from ethylacetate-hexane to yield 8.0 g of solid, m.p. 116°–118° C. It was then recrystallized from ethyl acetate isopropyl ether, to yield a solid, m.p. 123°–125° C.

Calc'd for $C_{15}H_{19}N_3O_3S_3$: C, 46.73; H, 4.97; N, 10.90. Found: C, 46.59; H, 4.90; N, 10.88.

EXAMPLE XV

Preparation of 2-[[O-[N-methyl-N-(4-tert-butylphenylthiosulfenyl)carbamoyl]oximino]]-3,5,5-trimethylthiazolidin-4-one.

2-[[O-[N-Methyl-N-(4-tert-butylphenylthiosulfenyl carbamoyl]oximino]]-3,5,5-trimethylthiazolidin-4-one was prepared according to the procedure described in Example I, by reacting 1.27 g (0.0073 m) of 3,5,5-trimethyl-2-oximinothiazolidin-4-one, 2.0 g (0.0073 m) of N-methyl-N-(4-tert-butylphenylthiosulfenyl) carbamoyl fluoride and 0.736 g (0.0073 m) of triethylamine in 25 ml of dioxane. 2-[[O-[N-Methyl-N-(4-tert-butylphenylthiosulfenyl)carbamoyl]oximino]]3,5,5-trimethylthiazolidin-4-one was crystallized from isopropyl ether to yield 1.12 g of a white solid m.p. 124°–125° C.

Calc'd for $C_{18}H_{25}N_3O_3S_3$: C, 50.56; H, 5.89; N, 9.83. Found: C, 50.30; H, 5.62; N, 9.95.

EXAMPLE XVI

Preparation of 2-[[O-[N-methyl-(4-chlorophenylthiosulfenyl)carbamoyl]oximino]]-3,5,5-trimethylthiazolidin-4-one 2-[[O-[N-Methyl-N-(4-chlorophenylthiosulfenyl)carbamoyl]oximino]]-3,5,5-trimethylthiazolidin-4-one was prepared according to the procedure described in Example I, by reacting 5.0 g (0.0287 m) of 3,5,5-trimethyl-2-oximinothiazolidin-4-one, 7.22 g (0.0287 m) of N-methyl-N-(4-chlorophenylthiosulfenyl)carbamoyl fluoride and 2.9 g (0.0287 m) of triethylamine in 50 ml of dioxane. 2-[[O-[N-Methyl-N-(4-chlorophenylthiosulfenyl)carbamoyl]oximino]]-3,5,5-trimethylthiazolidin-4-one was crystallized from isopropyl ether to yield 5.9 g of a white solid, m.p. 74°–76° C.

Calc'd for $C_{14}H_{16}ClN_3O_3S_3$: C, 41.42; H, 3.97; N, 10.35. Found: C, 41.23; H, 3.80; N, 10.29.

EXAMPLE XVII

Preparation of 2-[[O-[N-methyl-N-(tert-butylthiosulfenyl)carbamoyl]oximino]]-1,3-dithiolane 2-[[O-[N-Methyl-N-(tert-butylthiosulfenyl)carbamoyl]oximino]]-1,3-dithiolane was prepared according to the procedure described in Example I, by reacting 2.9 g (0.0214 m) of 2-oximino-1,3-dithiolane, 4.23 g (0.0214 m) of N-methyl-N-(tert-butylthiosulfenyl)carbamoyl fluoride and 2.17 g (0.0214 m) of triethylamine in 50 ml of dioxane. 2-[[O-[N-Methyl-N-tert-butylthiosulfenyl)carbamoyl]oximino]]-1,3-dithiolane crystallized from methylene chloride isopropyl ether to yield 4.0 g of a white solid. It was then recrystallized from ethyl acetate to yield a solid, m.p. 112°–114° C.

Calc'd for $C_9H_{16}N_2O_2S_4$: C, 34.59; H, 5.16; N, 8.97. Found: C, 34.51; H, 5.14; N, 8.95.

EXAMPLE XVIII

Preparation of 2-[[O-[N-methyl-N-(4-tert.butylphenylthiosulfenyl)carbamoyl]oximino]]-1,4-dithiane 2-[[O-[N-Methyl-N-(4-tert.butylphenylthiosulfenyl)carbamoyl]oximino]]-1,4-dithiane was prepared according to the procedure described in Example I, by reacting 1.09 g (0.0073 m) of 2-oximino-1,4-dithiane, 2.0 g (0.0073 m) of N-methyl-N-(4-tert.butylphenylthiosulfenyl)carbamoyl fluoride and 0.736 g (0.0073 m) of triethylamine in 25 ml of dioxane. Weight of the residual oil 1.95 g IR (Neat) 5.75µ (C=O). NMR (CDCl$_3$) 1.28δ(s), 9H, t-butyl; 3.10δ(s), 4H, (CH$_2$), 3.20δ(s), 3H, CH$_3$N; 3.52δ(s) 2H, CH$_2$; 7.37δ(d), $J_{AB}$=8.5 H$^z$ 2H and 7.54δ(d) $J_{BA}$=85 H$_z$, 2H. Aromatic.

Calc'd for $C_{16}H_{22}N_2O_2S_4$: C, 47.73; H, 5.51; N, 6.96. Found: C, 48.86; H, 5.80; N, 6.65.

EXAMPLE XIX

Preparation of N-Methyl-N(methylthiosulfenyl)carbamoyl Fluoride

To a solution of 7.59 g of hydrogen fluoride in 50 ml of toulene, cooled to −50° C. was added dropwise with stirring to 21.62 g of methylisocyanate. After stirring for 1 hour 55.0 g of methylthiosulfenyl chloride in 200 ml of toulene was added followed by dropwise addition of 38.3 g of triethylamine. The reaction temperature during the addition of base was maintained between 0° and 10° C. Stirring continued for an additional one hour after the addition of base was completed. The precipitated salt was filtered off and the filtrate concentrated under vacuo. Distillation yielded 16.7 g of N-methyl-N(methylthiosulfenyl)carbamoyl fluoride, b.p. 42° C./0.2 Torr, $N_D^{24}$ 1,509b Calc'd. for $C_3H_6FNOS_2$: C; 23.22, H, 3.89, N, 9.02. Found: C, 23.39, H, 4.18, N, 8.75 IR (Neat) 5.58 (C=O), 7.05, 7.77, 8.4, 8.6, 9.2, 9.35, 10.6, 11.4, and 14.35µ NMR (CDCl$_3$), δ2.69, (Singlet), 3H, CH$_3$S, δ3.28, (doublet), J=1.0 H$_z$ 3H, CH$_3$N.

The following compounds are representative of other compounds which can be prepared according to this invention by selecting appropriate starting materials for use in the procedure described above.

2-[[O-[N-methyl-N-(2-methyl-2-propanethiosulfenyl)-carbamoyl]oximino]]-3-isopropylthiazolidin-4-one.
2-[[O-[N-methyl-N-(2-methyl-2-propanethiosulfenyl)-carbamoyl]oximino]]-3-ethylthiazolidin-4-one.
2-[[O-[N-methyl-N-2(propanethiosulfenyl)carbamoyl]oximino]]-3-isopropyl-5,5-dimethylthiazolidin-4-one.
2-[[O-[N-methyl-N-(octadecylthiosulfenyl)carbamoyl]oximino]]-3,5,5-trimethylthiazolidin-4-one.
2-[[O-[N-(p-fluorophenyl)-N-(2-methylpropanethiosulfenyl)carbamoyl]oximino]]-3,5,5-trimethylthiazolidin-4-one.
2-[[O-[N-methyl-N-2(propanethiosulfenyl)carbamoyl]oximino]]-3,5,5-trimethylthiazolidin-4-one.
2-[[O-[N-methyl-N-(n-butylthiosulfenyl)carbamoyl]oximino]]-3,5,5-trimethylthiazolidin-4-one.
2-[[O-[N-methyl-N-(cyclohexylthiosulfenyl)carbamoyl]oximino]]-3,5,5-trimethylthiazolidin-4-one.
2-[[O-[N-methyl-N-(phenylthiosulfenyl)carbamoyl]oximino]]-3,5,5-trimethylthiozolidin-4-one.
2-[[O-[N-methyl-N-(4-methylphenylthiosulfenyl)carbamoyl]oximino]]-3,5,5-trimethylthiazolidin-4-one.
2-[[O-[N-methyl-N-(4-chlorophenylthiosulfenyl)carbamoyl]oximino]]-3,5,5-trimethylthiazolidin-4-one.
2-[[O-[N-methyl-N-(4-t-butylphenylthiosulfenyl)carbamoyl]oximino]]-3,5,5-trimethylthiazolidin-4-one.
2-[[O-[N-methyl-N-(4-t-butylphenylthiosulfenyl)carbamoyl]oximino]]-4,5,5-trimethylthiazolidin-3-one.
2-[[O-[N-methyl-N-(2-methyl-2-propanethiosulfenyl)-carbamoyl]oximino]]-4,5,5-trimethylthiazolidin-3-one.
2-[[O-[N-methyl-N-2(propanethiosulfenyl)carbamoyl]oximino]]-4,5,5-trimethylthiazolidin-3-one.
2-[[O-[N-methyl-N(n-butylthiosulfenyl)carbamoyl]oximino]]-1,4-dithiane-4,4-dioxide.
2-[[O-[N-methyl-N-(phenylthiosulfenyl)carbamoyl]oximino]]-1,4-dithiane-4-oxide.
2-[[O-[N-methyl-N-(4-t-butylphenylthiosulfenyl)carbamoyl]oximino]]-1,4-dithiane.
2-[[O-[N-methyl-N-(4-t-butylphenylthiosulfenyl)carbamoyl]oximino]]-3,3-dimethyl-1,4-dithiane.
2-[[O-[N-methyl-N-(2-methyl-2-propanethiosulfenyl)-carbamoyl]oximino]]-3,3-dimethyl-1,4-dithiane.
4-[[O-[N-methyl-N-(methylthiosulfenyl)carbamoyl]oximino]]-5-methyl-1,3-oxathiolane.
4-[[O-[N-methyl-N-(2-propanethiosulfenyl)carbamoyl]oximino]]-5-methyl-1,3-oxathiolane.
4-[[O-[N-methyl-N-(cyclohexylthiosulfenyl)carbamoyl]oximino]]-5-methyl-1,3-oxathiolane.
4-[[O-[N-methyl-N-(phenylthiosulfenyl)carbamoyl]oximino]]-5-methyl-1,3-oxathiolane.
4-[[O-[N-methyl-N-(4-methylphenylthiosulfenyl)carbamoyl]oximino]]-5-methyl-1,3-oxathiolane.
4-[[O-[N-methyl-N-(4-t-butylphenylthiosulfenyl)carbamoyl]oximino]]-5-methyl-1,3-oxathiolane.
4-[[O-[N-methyl-N-(4-chlorophenylthiosulfenyl)carbamoyl]oximino]]-5-methyl-1,3-oxathiolane.
2-[[O-[N-methyl-N-2(methyl-2-propanethiosulfenyl)-carbamoyl]oximino]]-1,3-dithiolane.
2-[[O-[N-methyl-N-(4-t-butylphenylthiosulfenyl)carbamoyl]oximino]]-1,3-dithiolane.
2-[[O-[N-methyl-N-(4-trifluoromethylphenylthiosulfenyl)carbamoyl]oximino]]-1,3-dithiolane.
4-[[O-[N-methyl-N-2(methyl-2-propanethiosulfenyl)-carbamoyl]oximino]]-1,3-dithiolane.
4-[[O-[N-methyl-N-(t-butylphenylthiosulfenyl)carbamoyl]oximino]]-1,3-dithiolane.
4-[[O-[N-methyl-N-2(2-methyl-2-propanethiosulfenyl)-carbamoyl]oximino]]-5-methyl-1,3-dithiolane.
4-[[O-[N-methyl-N-(4-t-butylphenylthiosulfenyl)carbamoyl]oximino]]-5-methyl-1,3-dithiolane.

4-[[O-[N-methyl-N-(2-methyl-2-propanethiosulfenyl)-carbamoyl]oximino]]-5,5-dimethyl-1,3-dithiolane.
4-[[O-[N-methyl-N-(4-t-butylphenylthiosulfenyl)carbamoyl]oximino]]-5,5-dimethyl-1,3-dithiolane.
3-[[O-[N-methyl-N-(4-t-butylphenylthiosulfenyl)carbamoyl]oximino]]-2-methyl-1,4-oxathiane
2-[[O-[N-methyl-N-(2-methyl-2-propanethiosulfenyl)carbamoyl]oximino]]-4-methyltetrahydro-1,4-thiazin-3-one.
2-[[O-[N-methyl-N-(4-t-butylphenylthiosulfenyl)carbamoyl]oximino]]-4-methyltetrahydro-1,4-thiazin-3-one.
2-[[O-[N-methyl-N-(4-chlorophenylthiosulfenyl)carbamoyl]oximino]]-4-isopropyltetrahydro-1,4-thiazin-3-one.
4-[[O-[N-methyl-N-(4-t-butylphenylthiosulfenyl)carbamoyl]oximino]]-2,2-dimethyl-1,3-dithiolane.
2-[[O-[N-methyl-(4-t-butylphenylthiosulfenyl)carbamoyl]oximino]]-1,3-oxathiolane.
2-[[O-[N-methyl-N-(2-methyl-2-propanethiosulfenyl)carbamoyl]oximino]]-1,3-oxathiolane.
2-[[O-[N-methyl-N-(2-methyl-2-propanethiosulfenyl)carbamoyl]oximino]]4-vinyl-1,3-dithiolane.
2-[[O-[N-methyl-N-(4-t-butylphenylthiosulfenyl)carbamoyl]oximino]]-4-vinyl-1,3-dithiolane.
2-[[O-[N-methyl-N-(4-t-butylphenylthiosulfenyl)carbamoyl]oximino]]thiophane.

Selected species of the new compounds were evaluated to determine their pesticidal activity against nematodes, mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°-70° F. and 50-70 percent relative humidity, constituted the test insects. For testing purposes, the number of aphids per pot was standardized to 100-150 by trimming plants containing excess aphids.

The test compounds were formulated by diluting the stock suspension with water to give a suspension containing 500 parts of test compound per million parts of final formulation.

The potted plants (one pot per compound tested) infested with 100-150 aphids, were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°-70° F. and 50-70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania*, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica*, L.) reared according to the specifications of the Chemical Specialties Manufacturing Association (Blue Book, McNair-Dorland Co., N.Y. 1954; pages 243-244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

Nematode Test

Infective migratory larvae of the root-knot nematode, (*Meloidogyne incognita* var. *acrita*) were reared in the greenhouse on roots of Rutgers variety tomato plant. Infected tomato plants were removed from the culture and the roots were chopped very finely. A small amount of inoculum from the roots was added to pint Mason jars containing approximately 180 cc of soil. The jars containing the inoculum and soil were capped and incubated for one week at room temperature. During this period eggs of the nematode hatched and the larvae forms migrated into the soil.

The test compounds were formulated by diluting the stock suspension with water to give a suspension containing 500 parts of test compound per million parts of final formulation. 10 milliliters of the test formulation was added to each of two jars for each dosage treated. As a control 10 milliliters of a water-acetone-emulsifier solution containing no test compound was also added to jars containing nematode larvae. The jars were capped and the contents thoroughly mixed on a kale mill for five minutes. The jars remained capped at room temperature for a period of 48 hours and the contents were then transferred to 3 inch pots. Subsequently, the pots were seeded to cucumber as an indicator crop and placed in the green house where they were cared for in the normal fashion for growing potted cucumber for approximately three weeks. These cucumber plants were then removed from the pots, the soil washed from the roots and the amount of galling visually rated.

The results of these tests are set forth in Table I below. In these tests the pesticidal activity of the compounds against aphid, mite, Southern Armyworm, Bean Beetle and house fly was rated as follows:

A=excellent control
B=partial control
C=no control

The nematocidal toxicity has the following ratings;
1=severe galling; equal to untreated control;
2=moderate galling
3=light galling
4=very light galling
5=no galling Dashes indicate no test conducted.

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of all of these tests are set forth in Table I below:

TABLE I

BIOLOGICAL ACTIVITY

| STRUCTURE | Aphid | Mite | S. Army-worm | M. Bean Beetle | H. Fly | Nema-todes | A O. Rat. mg/kg |
|---|---|---|---|---|---|---|---|
| (structure 1) | A | C | A | A | A | 1 | 299 |
| (structure 2) | A | A | A | A | A | 1 | — |
| (structure 3) | A | A | A | A | A | 1 | — |
| (structure 4) | A | A | A | A | A | 1 | — |
| (structure 5) | A | A | A | A | A | 1 | — |
| (structure 6) | A | A | A | A | A | 1 | — |
| (structure 7) | A | A | A | A | A | 2 | — |
| (structure 8) | A | A | A | A | A | 1 | — |
| (structure 9) | A | A | A | A | A | 1 | — |

TABLE I-continued

BIOLOGICAL ACTIVITY

| STRUCTURE | Aphid | Mite | S. Army-worm | M. Bean Beetle | H. Fly | Nema-todes | A O. Rat. mg/kg |
|---|---|---|---|---|---|---|---|
| [structure] | A | C | A | A | A | 1 | — |
| [structure] | A | A | A | A | A | 5 | — |
| [structure] | A | C | A | A | C | 2 | — |
| [structure] | A | C | A | A | B | 1 | — |
| [structure] | C | C | A | A | C | 1 | — |
| [structure] | C | C | A | A | C | 1 | — |
| [structure] | A | C | A | A | B | 1 | — |
| [structure] | A | C | A | A | A | 5 | 5.6 |

TABLE I-continued
BIOLOGICAL ACTIVITY

| STRUCTURE | Aphid | Mite | S. Army-worm | M. Bean Beetle | H. Fly | Nema-todes | A O. Rat. mg/kg |
|---|---|---|---|---|---|---|---|
| 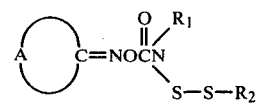 | A | A | A | A | A | 4 | — |

The compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pound of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount of kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants.

What is claimed is:

1. A compound of the formula:

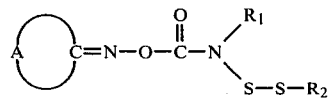

wherein:
$R_1$ is lower alkyl;
$R_2$ is alkyl, alkenyl, cycloalkyl, cycloalkenyl, bicycloalkyl, bicycloalkenyl, phenyl, phenylalkyl or phenyl or phenylalkyl substituted with one or more chloro, bromo, fluoro, nitro, cyano, alkyl, alkylthio, methylenedioxy, dialkylamino, trifluoromethyl, phenoxy, phenylthio substituents or a combination thereof;
A is a divalent aliphatic chain completing a five or six membered ring, which includes in any combination, one or two divalent oxygen, sulfur, sulfinyl, sulfonyl or amido group.

2. A compound of the formula:

wherein:
$R_1$ is lower alkyl;
$R_2$ is alkyl, alkenyl, cycloalkyl, cycloalkenyl, bicycloalkyl, bicycloalkenyl, phenyl, phenylalkyl or either phenyl or phenylalkyl substituted with one or more chloro, bromo, fluoro, nitro, cyano, alkyl, alkylthio, methylenedioxy, dialkylamino, trifluoromethyl, phenoxy, or phenylthio substituents,
A is a divalent aliphatic chain completing a six membered alicyclic ring which includes two divalent moieties selected from the group consisting of sulfur, sulfinyl and sulfonyl.

3. A compound according to claim 2 wherein A includes two divalent sulfurs.

4. A compound according to claim 2 wherein:
$R_1$ is alkyl having from 1 to 4 carbon atoms;
$R_2$ is alkyl having from 1 to 18 carbon atoms; cycloalkyl having from 3 to 8 carbon atoms or either substituted or unsubstituted phenyl or phenylalkyl including from 1 to 4 carbon aliphatic atoms.

5. A compound according to claim 2 wherein R₁ is methyl.

6. A compound according to claim 2 wherein R₂ is n-butyl, tert-butyl, isopropyl, cycloalkyl, tolyl or p-tert-butylphenyl.

7. 2-[[O-[N-methyl-N(4-t-butyl-phenylthiosulfenyl)-carbamoyl]oximino]]-1,4-dithiane.

8. 2-[[O-[N-methyl-N-(4-t-butyl-thiosulfenyl)carbamoyl]oximino]]-1,4-dithiane.

9. A miticidal, insecticidal and nematocidal composition comprising an acceptable carrier and as an active toxicant amiticidally, insecticidally and nematocidally effective amount of a compound of the formula

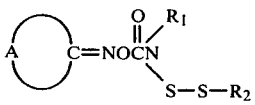

wherein:
R₁ is lower alkyl;
R₂ is alkyl, alkenyl, cycloalkyl, cycloalkenyl, bicycloalkyl, bicycloalkenyl, phenyl, phenylalkyl or phenyl or phenylalkyl substituted with one or more chloro, bromo, fluoro, nitro, cyano, alkyl, alkylthio, methylenedioxy, dialkylamino, trifluoromethyl, phenoxy, phenylthio substituents or a combination thereof;
A is a divalent aliphatic chain completing a five or six membered ring, which includes in any combination, one or two divalent oxygen, sulfur, sulfinyl, sulfonyl or amido.

10. A composition according to claim 9 wherein A is a divalent aliphatic chain completing a five or six membered alicyclic ring which includes one sulfur atom.

11. A composition according to claim 9 wherein A is a divalent aliphatic chain completing a five or six membered alicyclic ring which includes two divalent sulfurs.

12. A composition according to claim 9 wherein A is a divalent aliphatic chain completing a five or six membered alicyclic ring which includes one divalent oxygen atom and one divalent sulfur atom.

13. A composition according to claim 9 wherein A is a divalent aliphatic chain completing a five or six membered alicyclic ring which includes one divalent sulfur atom and one amido group.

14. A composition according to claim 9 wherein the active toxicant is 2-[[O -[N-methyl-N-(2-t-butyl thiosulfenyl)carbamoyl]oximino]]-1,3-dithiolane.

15. A composition according to claim 9 wherein the active toxicant is 4-[[O -[N-methyl-N-(4-t-butylthiosulfenyl)carbamoyl]oximino]]-5-methyl-1,3-oxathiolane.

16. A composition according to claim 9 wherein the active toxicant is 4-[[O -[N-methyl-N-(4-phenylthiosulfenyl)carbamoyl]oximino]]-5-methyl-1,3-oxathiolane.

17. A composition according to claim 9 wherein the active toxicant is 2-[[O -[N-methyl-N(phenylthiosulfenyl)carbamoyl]oximino]]-3,5,5-trimethylthiazolidin-4-one.

18. A composition according to claim 9 wherein the active toxicant is 2-[[O -[N-methyl-N-(cyclohexylthiosulfenyl)carbamoyl]oximino]]-3,5,5-trimethylthiazolidin-4-one.

19. An insecticidal, miticidal and nematocidal composition comprising an acceptable carrier and as the active toxicant a miticidally, insecticidally or nematocidally effective amount of a compound of the formula:

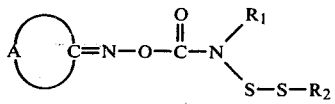

wherein:
A is a divalent aliphatic chain completing a six membered alicyclic ring which includes two divalent moieties selected from the group consisting of sulfur, sulfinyl and sulfonyl;
R₁ is lower alkyl;
R₂ is alkyl, alkenyl, cycloalkyl, cycloalkenyl, bicycloalkyl, bicycloalkenyl, phenyl, phenylalkyl or either phenyl or phenylalkyl substituted with one or more chloro, bromo, fluoro, nitro, cyano, alkyl, alkylthio, methylenedioxy, dialkylamino, trifluoromethyl, phenoxy, or phenylthio substituents.

20. A composition according to claim 19 wherein A includes two divalent sulfurs.

21. A composition according to claim 19 wherein:
R₁ is lower alkyl having from 1 to 4 carbon atoms;
R₂ is alkyl having from 1 to 18 carbon atoms, cycloalkyl having from 3 to 8 carbon atoms, phenyl, phenylalkyl including from 1 to 4 aliphatic carbons, substituted phenyl or substituted phenylalkyl.

22. A composition according to claim 19 wherein R₁ is methyl.

23. A composition according to claim 19 wherein R₂ is n-butyl, tert-butyl, isopropyl, cycloalkyl, tolyl or p-tert-butylphenyl.

24. A composition according to claim 19 wherein the active toxicant is 2-[[O -[N-methyl-N-(4-t-butylphenylthiosulfenyl)carbamoyl]oximino]]-1,4-dithiane.

25. A composition according to claim 19 wherein the active toxicant is 2-[[O -[N-methyl-N-(4-t-butylthiosulfenylcarbamoyl]oximino]]-1,4-dithiane.

26. A method of controlling insects, mites and nematodes which comprises subjecting them to a miticidally, insecticidally and nematocidally amount of a compound of the formula:

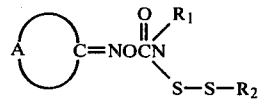

wherein:
R₁ is lower alkyl;
R₂ is alkyl, alkenyl, cycloalkyl, cycloalkenyl, bicycloalkyl, bicycloalkenyl, phenyl, phenylalkyl or phenyl or phenylalkyl substituted with one or more chloro, bromo, fluoro, nitro, cyano, alkyl, alkylthio, methylene dioxy, dialkylamino, trifluoromethyl, phenoxy, phenylthio substituents or a combination thereof;
A is a divalent aliphatic completing a five or six membered ring, which includes in any combination, one or two divalent oxygen, sulfur, sulfinyl, sulfonyl or amido group.

27. A method according to claim 26 wherein A is a divalent aliphatic chain completing a five or six membered alicyclic ring which includes one sulfur atom.

28. A method according to claim 26 wherein A is a divalent aliphatic chain completing a five or six membered alicyclic ring which includes two divalent sulfurs.

29. A method according to claim 26 wherein A is a divalent aliphatic chain completing a five or six membered alicyclic ring which includes one divalent oxygen atom and one divalent sulfur atom.

30. A method according to claim 26 wherein A is a divalent chain completing a five or six membered alicyclic ring which includes one divalent sulfur atom and one amido group.

31. A method according to claim 26 wherein the compound is 2-[[O-[N-methyl-N-(2-t-butylthiosulfenyl) carbamoyl]oximino]]-1,3-dithiolane.

32. A method according to claim 26 wherein the compound is 4-[[O-[N-methyl-N-(4-t-butylthiosulfenyl)carbamoyl]oximino]]-5-methyl-1,3-oxathiolane.

33. A method according to claim 26 wherein the compound is 4-[[O-[N-methyl-N-(4-phenylthiosulfenyl)carbamoyl]oximino]]-5-methyl-1,3-oxathiolane.

34. A method according to claim 26 wherein the compound is 2-[[O-[N-methyl-N-(phenylthiosulfenyl) carbamoyl]oximino]]-3,5,5-trimethylthiazolidin-4-one.

35. A method according to claim 26 wherein the compound is 2-[[O-[N-methyl-N-(cyclohexylthiosulfenyl)carbamoyl]oximino]]-3,5,5-trimethylthiazolidin-4-one.

36. A method of controlling insects, mites and nematodes which comprises subjecting them to an insecticidally, miticidally or nematocidally effective amount of a compound of the formula:

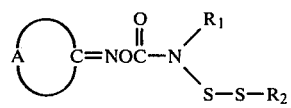

wherein:
R$_1$ is lower alkyl;
R$_2$ is alkyl, alkenyl, cycloalkyl, cycloalkenyl, bicycloalkyl, bicycloalkenyl, phenyl, phenylalkyl or either phenyl or phenylalkyl substituted with one or more chloro, bromo, fluoro, nitro, cyano, alkyl, alkylthio, methylenedioxy, dialkylamino, trifluoromethyl, phenoxy, or phenylthio substituents;
A is a divalent aliphatic chain completing a six membered alicyclic ring which includes two divalent moieties selected from the group consisting of sulfur, sulfinyl and sulfonyl.

37. A method according to claim 36 wherein A includes two divalent sulfurs.

38. A method according to claim 36 wherein;
R$_1$ is lower alkyl having from 1 to 4 carbon atoms;
R$_2$ is alkyl having from 1 to 18 carbon atoms, cycloalkyl having from 3 to 8 carbon atoms, phenyl, phenylalkyl including from 1 to 4 aliphatic carbons, substituted phenyl or substituted phenylalkyl.

39. A method according to claim 36 wherein R$_1$ is methyl.

40. A method according to claim 36 wherein R$_2$ is n-butyl, tert-butyl, isopropyl, cycloalkyl, tolyl or p-tert-butylphenyl.

41. A method according to claim 36 wherein the compound is 2-[[O-[N-methyl-N-(4-t-butylphenyl thiosulfenyl)carbamoyl]oximino]]-1,4-dithiane.

42. A method according to claim 36 wherein the compound is 2-[[O-[N-methyl-N-(4-t-butylthiosulfenyl)carbamoyl]oximino]]-1,4-dithiane.

* * * * *

UNITED STATES PATENT AND TRADEMARK OFFICE
CERTIFICATE OF CORRECTION

PATENT NO. : 4,232,035  Page 1 of 3
DATED : November 4, 1980
INVENTOR(S) : Themistocles D. J. D'Silva It is certified that error appears in the above—identified patent and that said Letters Patent is hereby corrected as shown below:

Column 2, line 5, "o" should read -- or --.

Column 2, line 49, "3,5,5-trimethylthiazo lidin-4-one." should read -- 3,5,5-trimethylthiazolidin-4-one. --.

Column 15, third structure under Table I,

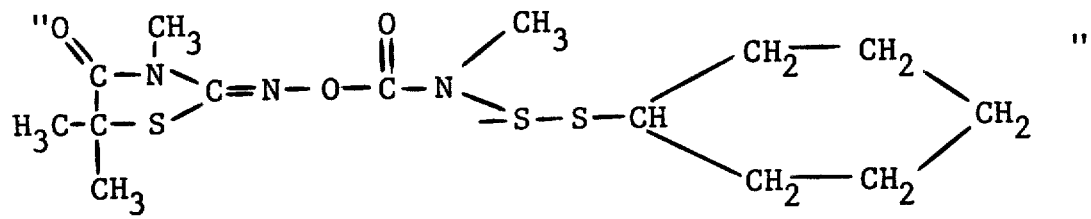

should read,

UNITED STATES PATENT AND TRADEMARK OFFICE
CERTIFICATE OF CORRECTION

PATENT NO. : 4,232,035           Page 2 of 3
DATED : November 4, 1980
INVENTOR(S) : Themistocles D. J. D'Silva It is certified that error appears in the above—identified patent and that said Letters Patent is hereby corrected as shown below:

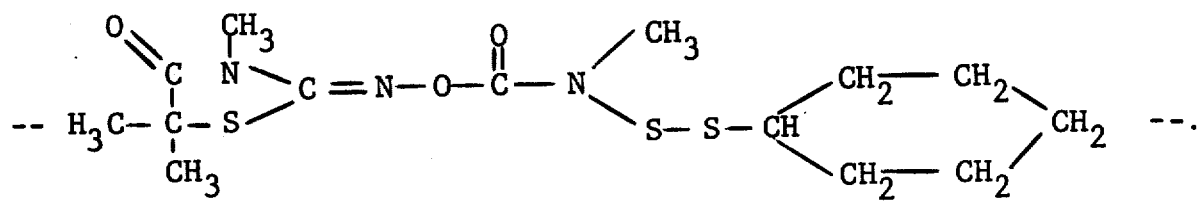

Column 19, lines 60 and 61, claim 17,

"2-[[O-[3N-methyl-N(phenylthiosulfenyl)" should read,

-- 2-[[O-[N-methyl-N(phenylthiosulfenyl) --.

Column 21, lines 16 and 17, claim 31,

"2-[[O-[N-methyl-N-(2-t-butyl Ɔ thiosulfenyl)" should read,

-- 2-[[O-[N-methyl-N-(2-t-butylthiosulfenyl) --.

Column 21, lines 20 and 21, claim 32,

"4-[[O-[N-methyl-N-(4-t-butyl Ɔ thiosulfenyl)" should read,

-- 4-[[O-[N-methyl-N-(4-t-butylthiosulfenyl) --.

UNITED STATES PATENT AND TRADEMARK OFFICE
CERTIFICATE OF CORRECTION

PATENT NO. : 4,232,035
DATED : November 4, 1980
INVENTOR(S) : Themistocles D. J. D'Silva It is certified that error appears in the above—identified patent and that said Letters Patent is hereby corrected as shown below:

Column 22, lines 36 and 37, claim 42,

"2-[[O-[N-methyl-N-(4-t-butyl thiosulfenyl)" should read,

-- 2-[[O-[N-methyl-N-(4-t-butylthiosulfenyl) --.

Signed and Sealed this

Twenty-ninth Day of September 1981

[SEAL]

Attest:

GERALD J. MOSSINGHOFF

Attesting Officer

Commissioner of Patents and Trademarks